US008974773B2

(12) United States Patent
Turmelle

(10) Patent No.: US 8,974,773 B2
(45) Date of Patent: Mar. 10, 2015

(54) DRYING, ANTI-SMEAR, AND ANTI-ODOR AGENT FOR SPRAY TANNING

(71) Applicant: Lindsay Turmelle, Encinitas, CA (US)

(72) Inventor: Lindsay Turmelle, Encinitas, CA (US)

(*) Notice: Subject to any disclaimer, the term of this patent is extended or adjusted under 35 U.S.C. 154(b) by 0 days.

(21) Appl. No.: 13/670,351

(22) Filed: Nov. 6, 2012

(65) Prior Publication Data
US 2013/0142738 A1 Jun. 6, 2013

Related U.S. Application Data

(60) Provisional application No. 61/557,868, filed on Nov. 9, 2011.

(51) Int. Cl.
A61K 8/25 (2006.01)
A61K 8/73 (2006.01)
A61Q 17/04 (2006.01)
A61K 8/64 (2006.01)
A61K 8/26 (2006.01)
A61Q 19/04 (2006.01)

(52) U.S. Cl.
CPC ... A61K 8/25 (2013.01); A61K 8/64 (2013.01); A61K 8/732 (2013.01); A61Q 17/04 (2013.01); A61K 8/26 (2013.01); A61Q 19/04 (2013.01); A61K 2800/884 (2013.01)
USPC ............... 424/59; 424/63; 132/200; 604/289

(58) Field of Classification Search
None
See application file for complete search history.

(56) References Cited

U.S. PATENT DOCUMENTS

| 2003/0118524 | A1* | 6/2003 | Karpov | 424/59 |
| 2003/0138533 | A1* | 7/2003 | Simmons | 426/321 |
| 2004/0234561 | A1* | 11/2004 | Ansmann et al. | 424/401 |
| 2008/0175803 | A1* | 7/2008 | Gordon | 424/59 |

OTHER PUBLICATIONS

Self Tanner (Tips on Applying Sunless Self Tanner, http://web.archive.org/web/20100630090542/http://getthebesttan.blogspot.com/2010/06/tips-on-applying-sunless-self-tanner.html, Internet Archive, Jun. 30, 2010).*
Cosmopolitan (How Do I . . . apply self tan?, http://www.cosmopolitan.co.uk/beauty-hair/news/styles/how-do-iapply-self-tan-99960, Internet Citation, Apr. 16, 2010).*

* cited by examiner

Primary Examiner — Rachael E Bredefeld
Assistant Examiner — Dominic Lazaro
(74) Attorney, Agent, or Firm — Mintz Levin Cohn Glovsky and Popeo, P.C.

(57) ABSTRACT

In some example embodiments, there is provided a method for sunless tanning. The method may include applying a sunless tanning solution to the skin and applying, during a drying stage of the sunless tanning solution, a powder to at least dry the tanning solution. Related compounds and methods may also be disclosed.

6 Claims, 1 Drawing Sheet

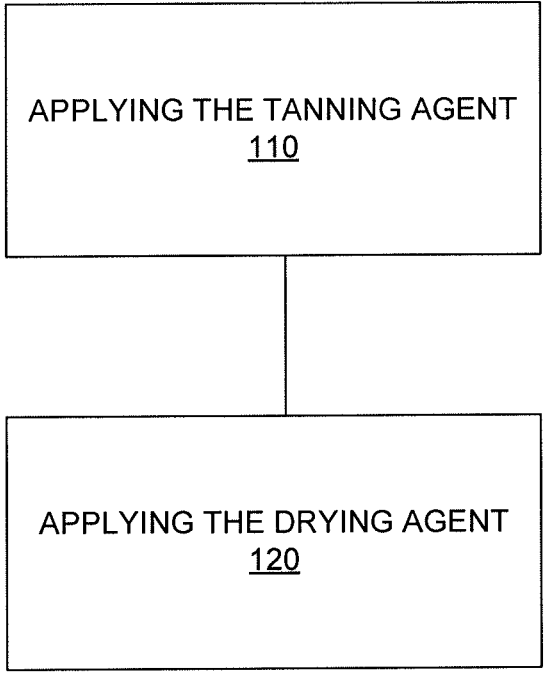

DRYING, ANTI-SMEAR, AND ANTI-ODOR AGENT FOR SPRAY TANNING

REFERENCE TO PRIORITY DOCUMENT

This application claims priority to U.S. Provisional Patent Application Ser. No. 61/557,868 entitled "DRYING AGENT FOR SPRAY TANNING," filed on Nov. 9, 2011, which is hereby incorporated by reference in its entirety.

BACKGROUND

Tanning of the human skin may occur by various methods including the sun bathing, artificial light, or via the use of tanning agents, such as compounds based on, for example, dihydroxyacetone (DHA), erythrulose, and the like. In the case of tanning agents, the tanning agent may be applied by a sprayer, such as for example, a handheld, airbrush sprayer or a booth. The sprayer may apply the tanning agent onto the skin of a subject undergoing a tanning treatment. For example, the handheld sprayer may be used to apply the tanning agent directly onto the skin of the subject undergoing the tanning treatment. The operator of the handheld sprayer may control the application of the tanning agent to induce the desired tanning effect on the subject. Once the operator completes the application of the tanning agent, the subject waits until the tanning agent dries to avoid smearing the tanning agent. When smearing occurs, the subject's tan appears uneven. Once the tanning process is complete, the subject may get dressed and resume normal, day-to-day activities, but with a tan obtained without having to be exposed to the harmful ultraviolet light of the sun or artificial light sources.

SUMMARY

In some example embodiments, methods, apparatus, and compounds are provided for a drying agent to enhance the drying of a tanning agent, to reduce the smearing of the tanning agent during the drying process, and/or to reduce, or eliminate, odor.

In some example embodiments, there is provided a method for sunless tanning. The method may include applying a sunless tanning solution to the skin; and applying, during a drying stage of the sunless tanning solution, a powder to at least dry the tanning solution.

In some example embodiments, there is provided a compound for drying a sunless tanning solution applied to the skin, the compound comprising a powder.

The details of one or more variations of the subject matter described herein are set forth in the accompanying drawings and the description below. Features and advantages of the subject matter described herein will be apparent from the description and drawings, and from the claims.

DESCRIPTION OF DRAWINGS

In the drawings,
FIG. 1 depicts a process for applying a drying agent.
Like references may be used where possible.

DETAILED DESCRIPTION

The subject matter described herein relates to a drying agent to enhance the drying process of a tanning solution (e.g., an agent) applied to the skin of a subject undergoing a spray tanning treatment. Although the application of a tanning agent enables a subject to obtain a tan without being exposed to harmful ultraviolet light from the sun or artificial light sources, once the tanning agent is applied, the subject may have to wait a considerable amount of time to ensure the tanning agent is dry. Otherwise, the subject risks damaging or smearing the tanning agent applied to the skin, which would result in a re-application of the tanning agent and thus further prolong the duration of the tanning treatment. To enhance the drying time of the tanning agent applied during the tanning treatment, the subject matter described herein provides, in some example embodiments, a drying agent to reduce the drying time of the tanning agent, to reduce the smearing of the tanning agent during the drying process, to reduce, or eliminate, odor during the drying process, and/or reduce stickiness of the skin during the drying process.

After the tanning agent is applied to the skin with a sprayer, such as a handheld, airbrush sprayer or an electronic tanning booth, the drying agent may be applied to reduce the overall drying time of the tanning agent, reducing thus the overall time required for a tanning treatment of a subject. The use of the drying agent as part of the tanning treatment may make the subject undergoing the tanning process feel dryer (i.e., less "sticky") after the application of the tanning agent. Moreover, the use of the drying agent as part of the tanning treatment may provide a fragrance to reduce any unpleasant odors associated with the tanning agent.

In some example embodiments, the drying agent may be implemented in powder form, although other types of implementations may be used as well. The drying agent powder may be applied with, for example, a brush, a powder puff, and/or any other type of applicator. For example, the drying agent may be applied as a powder by lightly applying the drying agent on the skin to avoid smearing the tanning agent on the skin. In some embodiments, the powder may also be applied using a spray mechanism, such as an airbrush sprayer or an aerosol sprayer.

In some example embodiments, the drying agent may be implemented as a powder comprising one or more of the following: talc, aluminum starch octenylsuccinate, cornstarch, tapioca starch, fragrance, silica, and clay (e.g., kaolin), and magnesium carbonate.

In some example embodiments, the drying agent may be implemented as a powder comprising one or more of the following: talc and fragrance.

In some example embodiments, the drying agent may be implemented as a powder comprising one or more of the following: silk powder, chlorphenesin, sodium Benzoate, mica, titanium dioxide, fragrance, and iron oxides.

In some example embodiments, the drying agent may be implemented as a powder comprising one or more of the following: about 42.55% talc, about 20% aluminum starch octenylsuccinate, about 10% zea mays starch, about 10% tapioca starch, about 6% fragrance, about 5% silica, about 4% kaolin, about 2% mica, iron oxides and/or titanium dioxides, about 0.01% silk powder, about 0.29% chlorphenesin, about 0.15% sodium benzoate.

In some example embodiments, the concentration of the talc varies from about 0 to about 90% of the overall composition of the drying agent.

In some example embodiments, the concentration of the aluminum starch octenylsuccinate varies from about 5% to about 75% of the overall composition of the drying agent.

In some example embodiments, the concentration of the zea mays starch varies from about 5% to about 70% of the overall composition of the drying agent.

In some example embodiments, the concentration of the tapioca starch varies from about 4% to about 80% of the overall composition of the drying agent.

In some example embodiments, the concentration of the fragrance varies from about 0% to about 15% of the overall composition of the drying agent.

In some example embodiments, the concentration of the silica varies from about 0% to about 20% of the overall composition of the drying agent.

In some example embodiments, the concentration of the kaolin varies from about 0% to about 30% of the overall composition of the drying agent.

In some example embodiments, mica, iron oxides, and/or titanium dioxides vary from about 0% to about 10% of the overall composition of the drying agent.

In some example embodiments, the concentration of the silk powder varies from about 0% to about 10% of the overall composition of the drying agent.

In some example embodiments, the concentration of the chlorphenesin varies from about 0% to about 1% of the overall composition of the drying agent.

In some example embodiments, the concentration of the sodium benzoate varies from about 0% to about 1% of the overall composition of the drying agent.

FIG. 1 depicts a process for applying a drying agent.

At 110, the tanning agent is applied to the skin. For example, a sprayer may be used to apply the tanning agent on the areas of the skin of a subject.

At 120, the drying agent powder is applied to the skin. For example, once the operator completes applying the tanning agent to the skin of the subject, the tanning agent is allowed to dry briefly (e.g., for about two minutes). After this brief drying, the drying agent is applied. For example, the operator may use a brush, powder puff, and the like to apply the drying agent. The drying agent may be in powder form, in which case the operator may lightly apply the drying agent powder over the skin areas that were the target of the tanning agent. The operator may also apply the drying agent powder to any creases, crevices, and folds of the skin that may be vulnerable to tanning agent smearing. In some implementations, the operator may apply the drying agent powder using, for example, a brush or a powder puff using gentle, light patting to avoid smearing the tanning agent on the skin. Next, the powdered skin of the subject is allowed to dry for an additional period of time, such as about 2 to 3 minutes, before the subject's tanning treatment is complete. When complete, the subject can, for example, resume normal activities, such as get dressed and the like, without smearing the tanning agent applied to the skin.

The subject matter may be implemented in systems, methods, and compounds. Although a few variations have been described in detail above, other modifications or additions are possible. In particular, further features and/or variations may be provided in addition to those set forth herein. For example, the implementations described above may be directed to various combinations and subcombinations of the disclosed features and/or combinations and subcombinations of several further features disclosed above. In addition, the logic flow depicted in the accompanying figures and/or described herein does not require the particular order shown, or sequential order, to achieve desirable results. Other embodiments may be within the scope of the following claims.

What is claimed:

1. A method for sunless tanning comprising:
applying a sunless spray tanning solution to skin; and
applying, during a drying stage of the sunless spray tanning solution applied to skin, a powder to at least facilitate drying of the applied sunless spray tanning solution, wherein the powder consists of a talc in a weight percentage range of less than or equal to approximately 90%, an aluminum starch octenylsuccinate in a weight percentage range of approximately 5% to 75%, a *zea mays* starch in a weight percentage range of approximately 5% to 70%, a tapioca starch in a weight percentage range of approximately 4% to 80%, a fragrance in a weight percentage range of less than or equal to approximately 15%, a silica in a weight percentage range of less than or equal to approximately 20%, a kaolin in a weight percentage range of less than or equal to approximately 30%, a silk powder in a weight percentage range of less than or equal to approximately 10%, a chlorphenesin in a weight percentage range of less than or equal to approximately 1%, a sodium benzoate in a weight percentage range of less than or equal to approximately 1%, and at least one of a titanium dioxide, a mica, and an iron oxide in a weight percentage range of less than or equal to approximately 10%.

2. A composition of matter for drying a sunless spray tanning solution applied to skin, the composition of matter consisting of a powder, wherein the power dries the applied sunless spray tanning solution application, the powder consisting of a talc in a weight percentage range of less than or equal to approximately 90%, an aluminum starch octenylsuccinate in a weight percentage range of approximately 5% to 75%, a *zea mays* starch in a weight percentage range of approximately 5% to 70%, a tapioca starch in a weight percentage range of approximately 4% to 80%, a fragrance in a weight percentage range of less than or equal to approximately 15%, a silica in a weight percentage range of less than or equal to approximately 20%, a kaolin in a weight percentage range of less than or equal to approximately 30%, a silk powder in a weight percentage range of less than or equal to approximately 10%, a chlorphenesin in a weight percentage range of less than or equal to approximately 1%, a sodium benzoate in a weight percentage range of less than or equal to approximately 1%, and at least one of a titanium dioxide, a mica, and an iron oxide in a weight percentage range of less than or equal to approximately 10%.

3. A method comprising:
applying a powder to a body to which a sunless spray tanning solution has previously been applied, wherein the applying the powder occurs during a drying phase about two minutes after the application of the sunless spray tanning solution to facilitate drying of the applied sunless spray tanning solution, the powder comprising a talc in a weight percentage range of less than or equal to approximately 90%, an aluminum starch octenylsuccinate in a weight percentage range of approximately 5% to 75%, a *zea mays* starch in a weight percentage range of approximately 5% to 70%, a tapioca starch in a weight percentage range of approximately 4% to 80%, a fragrance in a weight percentage range of less than or equal to approximately 15%, a silica in a weight percentage range of less than or equal to approximately 20%, a kaolin in a weight percentage range of less than or equal to approximately 30%, a silk powder in a weight percentage range of less than or equal to approximately 10%, a chlorphenesin in a weight percentage range of less than or equal to approximately 1%, sodium benzoate in a weight percentage fraction range of less than or equal to approximately 1%, and at least one of a titanium dioxide, a mica, and an iron oxide in a weight percentage range of less than or equal to approximately 10%.

4. The method of claim 1, wherein the applying during the drying stage comprises applying the powder at about two minutes after application of the sunless spray tanning solution to facilitate drying of the sunless spray tanning solution.

5. A method for applying a power during a sunless tanning process comprising:

applying a sunless spray tanning solution to skin; and applying, during a drying stage of the sunless spray tanning solution applied to skin, the powder to at least facilitate drying of the applied sunless spray tanning solution, wherein the powder consists of a talc having a weight percentage of approximately 42.55%, an aluminum starch octenylsuccinate having a weight percentage of approximately 20%, *zea mays* starch having a weight percentage of approximately 10%, a tapioca starch having a weight percentage of approximately 10%, a fragrance having a weight percentage of approximately 6%, a silica having a weight percentage of approximately 5%, a kaolin having a weight percentage of approximately 4%, a silk powder having a weight percentage of approximately 0.01%, a chlorphenesin having a weight percentage of approximately 0.29%, a sodium benzoate having a weight percentage of approximately 0.15%, and at least one of a titanium dioxide, a mica, and an iron oxide having a weight percentage of approximately 2%.

6. A composition of matter for drying a sunless spray tanning solution applied to skin, the composition of matter consisting of a powder, wherein the power dries the applied sunless spray tanning solution application, the powder consisting of a talc having a weight percentage of approximately 42.55%, an aluminum starch octenylsuccinate having a weight percentage of approximately 20%, *zea mays* starch having a weight percentage of approximately 10%, a tapioca starch having a weight percentage of approximately 10%, a fragrance having a weight percentage of approximately 6%, a silica having a weight percentage of approximately 5%, a kaolin having a weight percentage of approximately 4%, a silk powder having a weight percentage of approximately 0.01%, a chlorphenesin having a weight percentage of approximately 0.29%, a sodium benzoate having a weight percentage of approximately 0.15%, and at least one of a titanium dioxide, a mica, and an iron oxide having a weight percentage of approximately 2%.

\* \* \* \* \*